United States Patent [19]

Veber et al.

[11] Patent Number: 5,672,582

[45] Date of Patent: Sep. 30, 1997

[54] THROMBIN INHIBITORS

[75] Inventors: Daniel F. Veber, Ambler; S. Dale Lewis, Lansdale; Jules A. Shafer, Gwynedd Valley; Dong-Mei Feng, Harleysville, all of Pa.; Ruth F. Nutt, San Diego, Calif.; Stephen F. Brady, Philadelphia, Pa.

[73] Assignee: Merck & Co., Inc., Rahway, N.J.

[21] Appl. No.: 322,049

[22] Filed: Oct. 12, 1994

Related U.S. Application Data

[63] Continuation-in-part of Ser. No. 55,611, Apr. 30, 1993, abandoned.

[51] Int. Cl.[6] .................................................. A61K 38/05
[52] U.S. Cl. .......................... 514/19; 514/18; 530/331; 424/94.64; 562/445; 548/535
[58] Field of Search .......................... 514/18; 530/331; 424/94.64; 562/445; 548/535

[56] References Cited

FOREIGN PATENT DOCUMENTS

| 0363284 | 4/1990 | European Pat. Off. . |
| 0479489 | 4/1992 | European Pat. Off. . |
| 0 648 780 A1 | 8/1994 | European Pat. Off. . |

*Primary Examiner*—Howard E. Schain
*Assistant Examiner*—David Lukton
*Attorney, Agent, or Firm*—Richard S. Parr; Melvin Winokur

[57] ABSTRACT

4-substituted cyclohexylamine derivatives which are thrombin catalytic site inhibitors and which are useful as anticoagulants. These compounds show selectivity for thrombin over other trypsin-like enzymes and have oral bioavailability. They have the formula

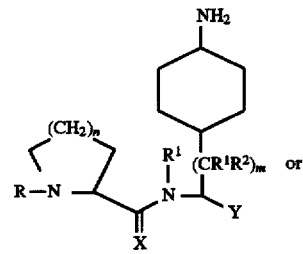

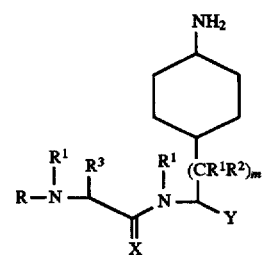

for example

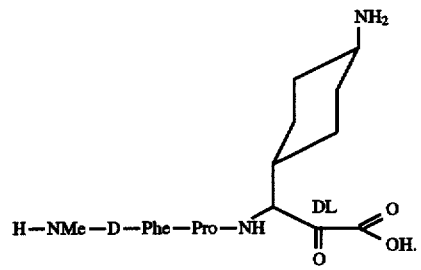

22 Claims, No Drawings

THROMBIN INHIBITORS

CROSS-REFERENCE TO RELATED APPLICATION

This application is a continuation-in-part of U.S. Ser. No. 08/055,611, filed Apr. 30, 1993 now abandoned.

BACKGROUND OF THE INVENTION

Thrombin is a serine protease present in blood plasma in the form of a precursor, prothrombin. Thrombin plays a central role in the mechanism of blood coagulation by convening the solution plasma protein, fibrinogen, into insoluble fibrin.

Edwards et al. *J. Amer. Chem. Soc.* (1992) vol. 114, pp. 1854–63, describes peptidyl α-ketobenzoxazoles which are reversible inhibitors of the serine proteases human leukocyte elastase and porcine pancreatic elastase. European Publication 363 284 describes analogs of peptidase substrates in which the nitrogen atom of the scissile amide group of the substrate peptide has been replaced by hydrogen or a substituted carbonyl moiety. Australian Publication 86245677 also describes peptidase inhibitors having an activated electrophilic ketone moiety such as fluoromethylene ketone or α-keto carboxyl derivatives.

Thrombin inhibitors described in prior publications show low selectivity for thrombin over other trypsin-like enzymes. Some of them show toxicity of hypotension and liver toxicity. Compounds of the s invention replace arginine and lysine with aminocyclohexyl moieties. These compounds show selectivity for thrombin over other trypsin-like enzymes and have oral bioavailability.

SUMMARY OF THE INVENTION

The invention comprises 4-substituted cyclohexylamine derivatives which are thrombin catalytic site inhibitors and which are useful as anticoagulants. These compounds show selectivity for thrombin over trypsin and other trypsin-like enzymes and have oral bioavailability. Trypsin-like enzymes (such as trypsin, thrombin, factor xa, kallikrein, plasmin, urokinase, and plasminogen activator) are serine dependent enzymes that catalyze hydrolysis at arginyl and lysyl peptide bonds.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAIL DESCRIPTION OF THE INVENTION

The invention includes compounds of the formula

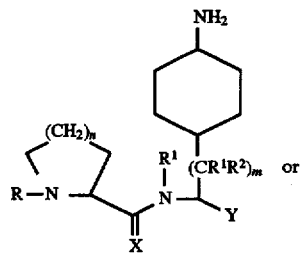

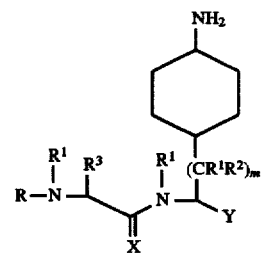

wherein:

m=0 or 1;

n=0, 1, or 2;

X=O or $H_2$;

R=arylsulfonyl, aminoacyl, acylaminoacyl, N-$C_{1-3}$alkyl aminoacyl, acyl-N-$C_{1-3}$alkylaminoacyl, arylacyl, aryl$C_{1-3}$alkanoyl, hydroxyacyl, aryloxycarbonyl, $C_{1-3}$alkyloxycarbonyl, or

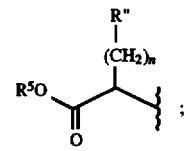

R''=aryl, heteroaryl, $C_{5-11}$ carbomonocyclic, or $C_{5-11}$carbobicyclic;

$R^1$=H or $CH_3$;

$R^2$=H or $CH_3$;

$R^3$=H, $C_{1-3}$alkyl, hydroxy$C_{1-3}$alkyl, carboxy$C_{1-3}$alkyl, amino$C_{1-3}$alkyl, guanido$C_{1-3}$alkyl, aryl or substituted aryl, arylmethyl, $C_{3-8}$ cycloalkylmethyl, or $C_{3-8}$ cycloalkyl;

Y=CHO, $COCF_3$, $BO_2R^7R^8$, $CO_2R^4$, COOH, $CONR^5R^6$, $COCO_2R^4$, $COCO_2H$, COCO—Q, or CO—W, wherein Q=a natural amino acid, cyclohexyl amino acid, $NR_5R^6$, or

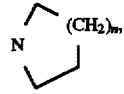

or derivative thereof; and

W=5–10 membered heterocyclic groups or substituted heterocyclic groups including, for example, tetrazole, furan, oxazole, benzoxazole, and imidazole;

$R^4$=$C_{1-3}$alkyl or aryl$C_{1-3}$alkyl;

$R^5$=H, $C_{1-3}$alkyl or aryl$C_{1-3}$alkyl;

$R^6$=H, $C_{1-3}$alkyl or aryl$C_{1-3}$alkyl;

$R^7$=H, $C_{1-3}$alkyl or aryl$C_{1-3}$alkyl; and $R^8$=H, $C_{1-3}$alkyl or aryl$C_{1-3}$alkyl, and pharmaceutically acceptable salts thereof.

In one class of compounds of the invention, the compounds have the formula

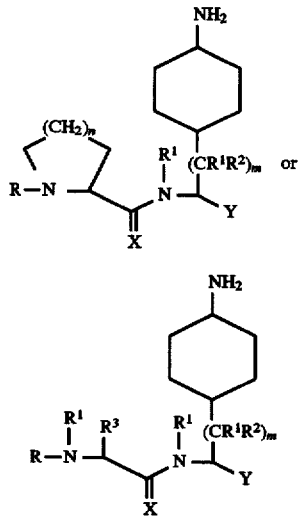

wherein:

n=0, 1, or 2;

m=0 or 1;

R=D-phenylalanine, D-Nal1, D-Nal2, D-cyclohexylalanine, D-tyrosine, β-3-benzothienyl-D-alanine, D-3,4-Cl$_2$-phenylalanine, 3-phenylpropionyl, 3,4-dichlorophenylpropionyl, 3-cyclohexylpropionyl, 3,3-diphenylpropionyl, 5-dicyclohexylpropionyl, and 9-hydroxyfluorene-9-carboxy, or N-methyl derivatives thereof, or

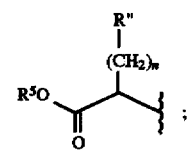

$R_1$=H;

$R^3$=H or cyclohexyl;

X=O or $H_2$; and

Y=CONH$_2$, COCO$_2$H, COCONHCH$_3$, COCONHCH$_2$Ph,

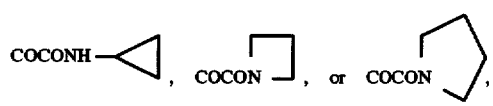

and pharmaceutically acceptable salts thereof.

Preferably, compounds of the invention have the formula

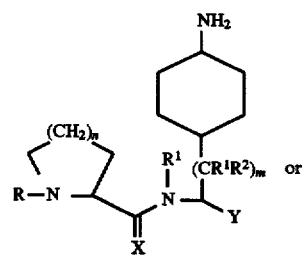

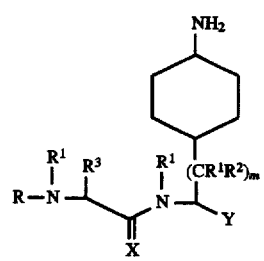

wherein:

n=0, 1, or 2;

m=0 or 1;

R=D-phenylalanine, D-Nal1, D-Nal2, D-cyclohexylalanine, D-tyrosine, β-3-benzothienyl-D-alanine, or D-3,4-Cl$_2$-phenylalanine, or N-methyl derivatives thereof, or

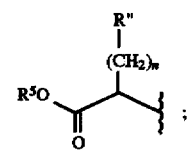

$R^1$=H;

$R^3$=H or cyclohexyl;

X=O or $H_2$; and

Y=CONH$_2$, COCO$_2$H, COCONHCH$_3$, COCONHCH$_2$Ph,

and pharmaceutically acceptable salts thereof.

More preferably, compounds of the invention have the formula

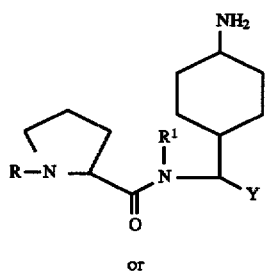

or

-continued

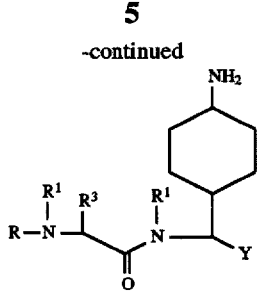

wherein:

R=N-methyl-D-phenylalanine, N-methyl-2-naphthyl-D-alanine, N-methyl-1-naphthyl-D-alanine, N-methyl-D-cyclohexylalanine, N-methyl-D-3,4-Cl$_2$-D-phenylalanine, or

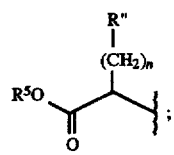

R$^1$=H;
R$^3$=H, cyclohexyl; and
Y=CONH$_2$, COCO$_2$H, COCONHCH$_3$,

or

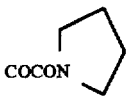

and pharmaceutically acceptable salts thereof.

Preferred embodiments of the invention are shown in the following table.

TABLE 1

| STRUCTURE | P$_1$ | Ki (μM) Thrombin | Trypsin | Ratio |
|---|---|---|---|---|
| (i) D—Phe—Pro—NH—CH(CH$_2$-cyclohexyl-NH$_2$)—C(O)NH$_2$ | t-Aca | 18.6 | 313 | 17 |
| (ii) D—Phe—Pro—NH—CH(cyclohexyl-NH$_2$)—C(O)NH$_2$ | L-t-Acg | 43 | 408 | 9 |
| (iii) D—Phe—Pro—NH—CH(cyclohexyl-NH$_2$)—C(O)NH$_2$ | D-t-Acg | 3 | 800 | 267 |
| (iv) H—NMe—D—Phe—Pro—NH—CH(CH$_2$-cyclohexyl-NH$_2$)—C(O)C(O)OH | L-t-Aca | 9.4 | 420 | 45 |

TABLE 1-continued

| STRUCTURE | P₁ | Ki (μM) | | |
| --- | --- | --- | --- | --- |
| | | Thrombin | Trypsin | Ratio |
| (v) H—NMe—D—Phe—Pro—NH-[cyclohexyl-CH₂-CH(DL)-C(=O)-OH with NH₂] | DL-t-Acg | 0.05 | 51 | 1000 |
| (vi) H—NMe—D—Phe—Pro—NH-[cyclohexyl-CH₂-CH-C(=O)-NHCH₃ with NH₂] | L-t-Aca | 52 | 1440 | 28 |
| (vii) H—NMe—D—Phe—Pro—NH-[cyclohexyl-CH₂-CH(A)-C(=O)-NHCH₃ with NH₂] | D-t-Acg | 3.3 | 7000 | 2121 |
| (viii) H—NMe—D—Phe—Pro—NH-[cyclohexyl-CH₂-CH(B)-C(=O)-NHCH₃ with NH₂] | L-t-Acg | 0.09 | 1151 | 12790 |

Assay for Determining Proteinase Inhibition

Assays of human α-thrombin and bovine trypsin were performed at 25° C. in 0.05M TRIS buffer pH 7.4, 0.15M NaCl, 0.1% PEG. Trypsin assays also contained 1 mM CaCl₂.

In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin ($K_m$=125 μM) and bovine trypsin ($K_m$=125 μM). "Sar" is the three letter abbreviation for the amino acid sarcosine (N-methylglycine). p-Nitroanilide substrate concentration was determined from measurements of absorbance at 342 nm using an extinction coefficient of 8270 cm⁻¹M⁻¹.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc ($K_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm (extinction coefficient=12600 cm⁻¹M⁻¹) of the 7-amino-4-trifluoromethyl coumarin produced upon complete hydrolysis of an aliquot of the stock solution by thrombin.

Activity assays were performed by diluting a stock solution of substrate at least tenfold to a final concentration <0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [S]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. Formulation and administration procedures are described following the Examples section.

Using the assays described above, the following additional embodiments of the invention were evaluated and shown to be selective for inhibiting thrombin. The constants were determined at pH 7.4 in buffer containing 0.05M Tris, 0.15M NaCl, 0.1% PEG-8000 at room temperature. "ni" denotes $K_i > 10$ μM.

TABLE 2

| Structure | Ki (nM) | |
|---|---|---|
| | Thrombin | Trypsin |
| (ix) | 4 | ni |
| (x) | 0.07 | 310 |
| (xi) | 0.4 | ni |

TABLE 2-continued

| Structure | Ki (nM) | |
|---|---|---|
| | Thrombin | Trypsin |
| (xii) | 0.025 | 660 |
| (xiii) | 2.2 | 4000 |
| (xiv) | 0.09 | 2100 |
| (xv) | 0.03 | 2000 |

TABLE 2-continued
| Structure | Ki (nM) | |
|---|---|---|
| | Thrombin | Trypsin |
| (xvi) 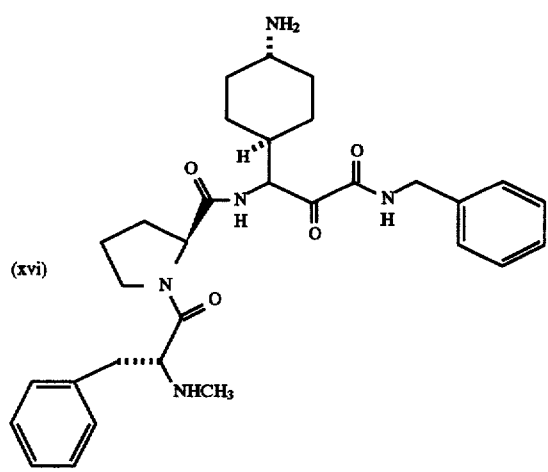 | 0.6 | 120 |
| (xvii) 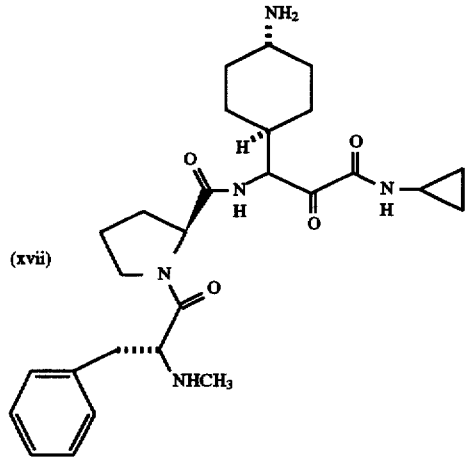 | 0.07 | 120 |
| (xviii) 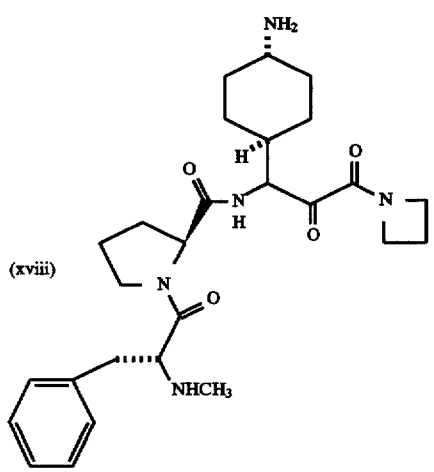 | 0.04 | 760 |

TABLE 2-continued

| Structure | Ki (nM) | |
|---|---|---|
| | Thrombin | Trypsin |
| (xix) | 0.2 | 8100 |
| (xx) | 0.04 | 66 |

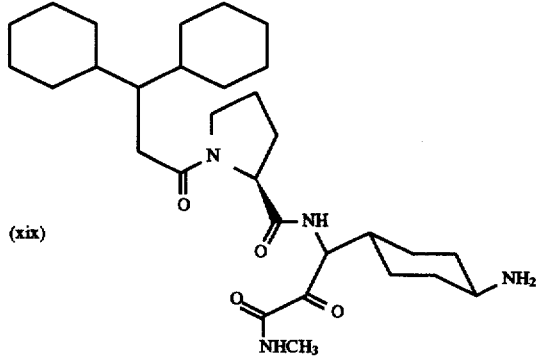

Table 3 shows the inhibitory effect of compounds listed in Tables 1 (compounds i–viii) and 2 (compounds ix–xx) on Factor Xa (fXa), plasma kallikrein (p-Kal), plasmin (Pl), tissue plasminogen activator (t-PA), and activated protein C (APC), using a chromogenic assay similar to the one described for evaluating the inhibitory effect on thrombin and on trypsin. "ni" denotes $K_i$>10 µM. The results further demonstrate the selectivity of compounds of the invention for inhibiting thrombin.

TABLE 3

| Structure | Ki (nM) | | | | |
|---|---|---|---|---|---|
| | fXa | p-Kal | Pl | tPA | APC |
| v | ni | 7000 | ni | ni | ni |
| viii | ni | ni | ni | ni | ni |
| ix | ni | ni | ni | ni | ni |
| x | 3000 | ni | 6000 | ni | ni |
| xi | ni | ni | ni | ni | ni |
| xii | 2300 | ni | ni | ni | ni |
| xiii | ni | ni | ni | ni | ni |
| xiv | 9000 | ni | ni | ni | ni |
| xv | ni | ni | ni | ni | ni |
| xvi | ni | ni | ni | ni | ni |
| xvii | ni | 9000 | ni | ni | ni |
| xviii | ni | ni | ni | ni | ni |
| xix | ni | ni | ni | ni | ni |
| xx | ni | ni | ni | ni | ni |

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues (aminoacyl functionalities) can also be modified by amidation, acylation or other substitution, which can, for example, change the solubility of the compounds without affecting their activity.

In the peptides shown, each residue, where appropriate, is represented by its three letter designation, corresponding to the trivial name of the amino acid. In addition to the abbreviations commonly used to represent natural amino acids, the abbreviation for naphthylalanine, Nal, is also used, e.g. D-Nal1, D-Nal2. Nal1refers to the amino acid where the beta carbon of alanine is attached to the 1-naphthyl position, and Nal2 refers to the amino acid where the beta carbon of alanine is attached to the 2-naphthyl position.

The term "aryl" refers to a mono- or polycyclic ring system composed of 5- and 6-membered aromatic rings containing 0, 1, or 2 heteroatoms chosen from N, O, or S. Term "acyl" refers to an alkylcarbonyl, cycloalkylcarbonyl, or arylcarbonyl group.

Other common abbreviations used in the examples have the following meanings: Boc is t-butyloxycarbonyl; Bzl is benzyl; Cbz is carbobenzyloxy; Chx is cyclohexyl; Aca is trans-4-aminocyclohexylalanine; and Acg is trans-4-aminocyclohexylglycine.

In the specific peptides shown in the present application, the L-form of any amino acid residue having an optical isomer is intended unless the D-form is expressly indicated.

EXAMPLE 1

Boc-NMe-D-Phe-Pro-OBzl (1—1)

To a solution of Boc-NMe-D-Phe-OH (7.0 g, 25 mmol) and H-Pro-OBzl.HCl (6.66 g, 27.5 mmol) in 200 ml of DMF was added 4.6 g (30 mmol) of HOBt.H$_2$O, the pH of the solution was adjusted to 8 (moist narrow pH paper), and EDC (6.47 g, 33.8 mmol) was added with magnetic stirring. After 3.5 hrs. the reaction was quenched by the addition of 50 ml of water. After keeping the mixture at room temperature for 16 hrs, the solvents were evaporated at reduced pressure and the residue was dissolved in EtOAc-H$_2$O. Aqueous KHSO$_4$ was added to this two-phase mixture and the layers were separated. The organic layer was extracted with NaHCO$_3$, saturated NaCl, and dried over MgSO$_4$. The solvent was evaporated to give product as a white solid which was further purified by chromatography using two columns of 600 g silica gel 60 (E. Merck) each and eluting with EtOAc-hexane (3:7). Fractions containing product were combined to give 11.3 g (97% yield) of 1—1.

TLC: R$_f$=0.65, silica gel, EtOAc-hexane (2:3)

In a similar manner are prepared the following:

PhCH$_2$CH$_2$CO-Pro-OBzl (1—1-1), by coupling of PhCH$_2$CH$_2$COOH with H-Pro-OBzl.HCl.

3,4-Dichloro-PhCH$_2$CH$_2$-Pro-OBzl (1—1-2), by coupling of 3,4-dichloro-PhCH$_2$CH$_2$—COOH with H-Pro-OBzl.HCl.

ChxCH$_2$CH$_2$CO-Pro-OBzl (1—1-3), by coupling of ChxCH$_2$CH$_2$COOH with H-Pro-OBzl.HCl.

Ph$_2$CHCH$_2$CO-Pro-OBzl (1—1-4), by coupling of Ph$_2$CHCH$_2$COOH with H-Pro-OBzl.HCl.

(Chx)$_2$CHCH$_2$CO-Pro-OBzl (1—1-5), by coupling of (Chx)$_2$CHCH$_2$COOH with H-Pro-OBzl.HCl.

9-Hydroxyfluorene-9-carboxy-Pro-OBzl (1—1-6), by coupling of 9-hydroxyfluorene-9-carboxylic acid with H-Pro-OBzl.HCl.

Boc-NMe-D-Phe-Pro-OH (1-2)

A solution of Boc-NMe-D-Phe-Pro-OBzl (1-1) (11.3 g) in 600 ml of 95% EtOH was flushed with N$_2$ three times and 1.8 g of 10% Pd/C was added under N$_2$. The mixture was evacuated, H$_2$ was introduced and the reaction mixture was kept under a H$_2$ atmosphere (balloon filled with H$_2$) for 50 min. The mixture was purged with N$_2$, filtered through Celite, and the filtrate was evaporated in vacuo. The viscous oil was flushed several times with CHCl$_3$ to yield a foamy white solid 1-2 (9.13 g, 100% yield).

TLC: R$_f$=0, silica gel, EtOAc-hexane (2:3); R$_f$=0.3, CHCl$_3$—MeOH—H$_2$O (90-10-1)

In a similar manner are prepared the following:

PhCH$_2$CH$_2$CO-Pro-OH (1-2-1), by reduction of PhCH$_2$CH$_2$CO-Pro-OBzl.

3,4-Dichloro-PhCH$_2$CH$_2$-Pro-OH (1-2-2), by reduction of 3,4-dichloro-PhCH$_2$CH$_2$-Pro-OBzl.

ChxCH$_2$CH$_2$CO-Pro-OH (1-2-3), by reduction of ChxCH$_2$CH$_2$CO-Pro-OBzl

Ph$_2$CHCH$_2$CO-Pro-OH (1-2-4), by reduction of Ph$_2$CHCH$_2$CO-Pro-OBzl.

(Chx)$_2$CHCH$_2$CO-Pro-OH (1-2-5), by reduction of ((Chx)$_2$CHCH$_2$CO-Pro-OBzl.

9-Hydroxyfluorene-9-carboxy-Pro-OH (1-2-6), by saponification of 9-Hydroxyfluorene-9-carboxy-Pro-OBzl.

EXAMPLE 2

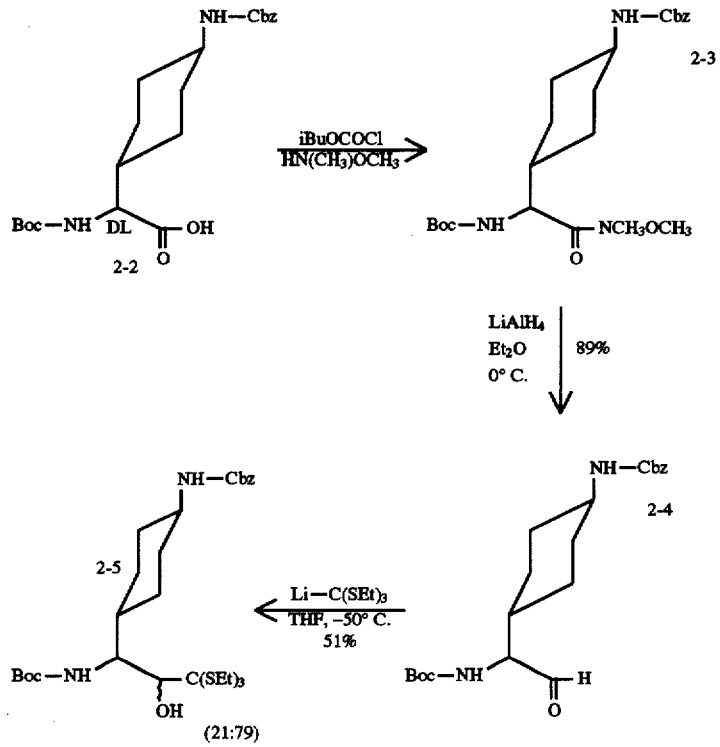

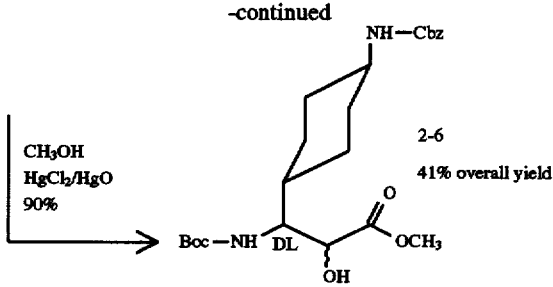

In the following description, "Acg" refers to 4-aminocyclohexylglycine.

Boc-trans-DL-Acg-OH (2-1)

According to Nutt et al., Peptides: Structure and Function, Proceed. of the 9th Amer. Pept. Symp., eds. C. Deber et al., Pierce Chemical Co. Rockford, Ill., 441–444 (1985), 2-1 was obtained. Banfi et al., Syn. Commun. 19 (9&10), 1787–1799 (1989) also describe the synthesis of the unprotected amino acid trans-DL-Acg-OH.

Boc-trans-DL-Acg(Cbz)-OH (2—2)

2-1 was Cbz-protected according to the procedure in Nutt et al. to give Boc-trans-DL-Acg(Cbz)-OH (2—2).

Boc-trans-DL-Acg(Cbz)-NMeOMe 2-3

To a suspension of Boc-trans-Acg(Cbz)-OH (2—2) (794 mg, 1.94 mmol) in $CH_2Cl_2$ (10 ml) was added N-methyl morpholine (NMM, 0.22 ml). After stirring magnetically for 15 min, all starting material had gone into solution. The temperature was lowered to $-15°$ C. and i-butyl chloroformate (0.25 ml, 0.27 g) was added. The mixture was stirred for 10 min and predried HNMeOMe.HCl (0.22 g) was added, followed by NMM (0.15 ml initially, 0.17 ml in increments over the next 40 min.). The reaction mixture was allowed to warm to room temperature and stirred for 18 hrs. Water was added to the reaction and after stirring for 30 min, $CH_2Cl_2$ was added and the organic layer washed with 1×$KHSO_4$ solution, 1×$H_2O$, 1×$NaHCO_3$ solution, and 2×50% saturated NaCl. The organic layer was dried over $Na_2SO_4$, filtered and evaporated to give 2-3 (746 mg, 85% yield). From the $NaHCO_3$ extract, starting material (101 mg, 12.7%) was recovered.

TLC: $R_f$=0.75, silica gel, $CHCl_3$—MeOH—$H_2O$ (95-5-0.5)

HPLC: retention times=19.43 min, (Vydac $C_{18}$, gradient of 95% A/B to 5% A/B over 30 min, A=0.1% TFA—$H_2O$, B=0.1% TFA—$CH_3CN$ NMR: $CD_3OD$, δ 7.4 (m,5), 5.1 (s,2), 4.5 (br m,1), 3.0 (s,3), 3.3 (MeOH), 3.2 (s,3), 1.95(m,2), 1.85 (m,1), 1.62(m, 2), 1.45 (s,9), 1.1–1.3 (m,4).

Boc-trans-DL-Acg(Cbz)Ψ[CHO] (2-4)

Into a dried flask equipped with mechanical stirrer, thermometer, and septum was added 616 mg (1.37 mmol) of Boc-t-Acg(Cbz)-NMeOMe (23) and 18 ml of dry THF. The suspension was cooled to $-40°$ C. and the LAH solution (1.78ml of 1M LAH in THF) was added dropwise at a rate to keep the reaction temperature below $-30°$ C. The resultant solution was stirred at $-5°$ C. for 50 min, then cooled to $-35°$ C. Ether (15 ml) and an aqueous solution of $KHSO_4$ were added keeping the temperature at $-15°$ C. The two layer mixture was stirred at room temperature for 30 min, the layers were separated and the aqueous layer was extracted twice with ether. The combined ether layers were extracted once with cold 1N HCl (3 ml), cold 5% $NaHCO_3$ solution (3 mL), and saturated NaCl solution (3 ml). The ether layer was dried over anhydrous $MgSO_4$, filtered, and evaporated in vacuo to yield 477 mg (89% yield) of (2–4).

TLC: $R_f$=0.7, silica gel, EtOAc-hexane (3:2)

HPLC: retention time 18.8 min; $C_{18}$, 100% A to 70% A/B over 30 min, A=0.1% TFA—$H_2O$, B=0.1% TFA—$CH_3CN$ NMR: $CDCl_3$, δ 9.62 (s,1,), 7.4 (m,5), 5.1 (m,3), 4.58 (d,1), 4.25 (t, 1), 3.42 (m,1), 2.1(m,2), 1.9 (m,2), 1.62(m,1), 1.58(broad, $H_2O$) 1.42 (s,9), 1.25(m,2), 1.18 (m,2).

Boc-trans-DL-Acg(Cbz)Ψ[CHOHC(SEt)$_3$] (2-5)

To a dry 100-ml 3-neck flask equipped with thermometer, magnetic stirrer, and addition funnel was added under $N_2$ triethylthioorthoformate (1.65 ml, 8.43 mmol) in dry THF (15 ml). The solution was cooled to $-65°$ C. and BuLi in THF (2.89 ml, 7.23 mmol) was added dropwise at a rate to keep the temperature below $-50°$ C. The reaction solution was stirred at $-60°$ C. for 30 min, and a solution of Boc-trans-Acg(Cbz)Ψ[CHO] (2-4) (470 mg, 1.2 mmol) in THF (4 ml) was added dropwise keeping the reaction solution at $-55°$ C. The addition funnel was washed with two 1-ml portions of THF. After stirring at $-40°$ C. for 2 hrs, a solution of $NH_4Cl$ (0.6 g) in $H_2O$ (13.5 ml) and ether (27 ml) were added, and the reaction mixture was allowed to warm to 10° C. The two layers were separated and the aqueous layer was extracted twice with ether. The combined ether layers were washed once with saturated NaCl solution, dried over $Na_2SO_4$, filtered, and evaporated in vacuo to give an oily residue. Product was isolated by chromatography using 90 g of silica gel (E. Merck 230–400 mesh) and EtOAc-hexane (3:9) as elution solvent. Fractions containing product ($R_f$=0.3, EtOAc-hexane 3:7) were combined and the solvent was removed by evaporation to give 2—5 (317 mg, 45% yield).

TLC: $R_f$=0.3, silica gel, EtOAc-hexane (3:7)

HPLC: retention times=25.25 min and 25.72 min, ratio 1:4, (Vydac $C_{18}$, gradient of 80% A/B to 10% A/B over 30 min, A=0.1% TFA—$H_2O$, B-0.1% TFA—$CH_3CN$ retention times=26.95 min and 27.36 min, ratio 1:4, (Vydac $C_{18}$, gradient of 95% A/B to 5% A/B over 30 min

Boc-trans-DL-Acg(Cbz)Ψ[CHOHCO]—OMe (2-6)

To a solution of Boc-trans-Acg(Cbz)Ψ[CHOHC(SEt)$_3$] (2-5) (310 mg, 0.528 mmol) in MeOH—$H_2O$ (18 ml, 17:1) was added under $N_2$ with magnetic stirring HgO (183 mg, 0.845 mmol) and $HgCl_2$ (674 mg, 2.48 mmol). The reaction mixture was stirred at room temperature for 1.5 hr and at 60° C. for 30 min. After cooling to room temperature, the reaction mixture was filtered through Celite, the Celite was washed with two 1-ml portions of MeOH, and three 5-ml portions of CH$_2$Cl$_2$. To the filtrate was added H$_2$O (20 ml) and CH$_2$Cl$_2$ (10 ml), the layers were separated and the aqueous layer was extracted two times with CH$_2$Cl$_2$ (20 ml). To the combined organic layers was added 70% NH$_4$OAc in H$_2$O the CH$_2$Cl$_2$ layer was removed from the three-phase mixture, the remaining mixture was extracted two times with CH$_2$Cl$_2$, the combined organic layers were washed once with saturated NH$_4$Cl solution, driedf with MgSO$_4$, filtered, and evaporated in vacuo to give 2-6 (215 mg, 90.4% yield).

TLC: R$_f$=0.4(major), 0.35(minor), silica gel, EtOAc-hexane (1:1)

HPLC: retention times=18.67 min and 19.02 min, ratio 1:4, (Vydac C$_{18}$, gradient of 95% A/B to 5% A/B over 30 min, A=0.1% TFA—H$_2$O, B=0.1% TFA—CH$_3$CN

EXAMPLE 3

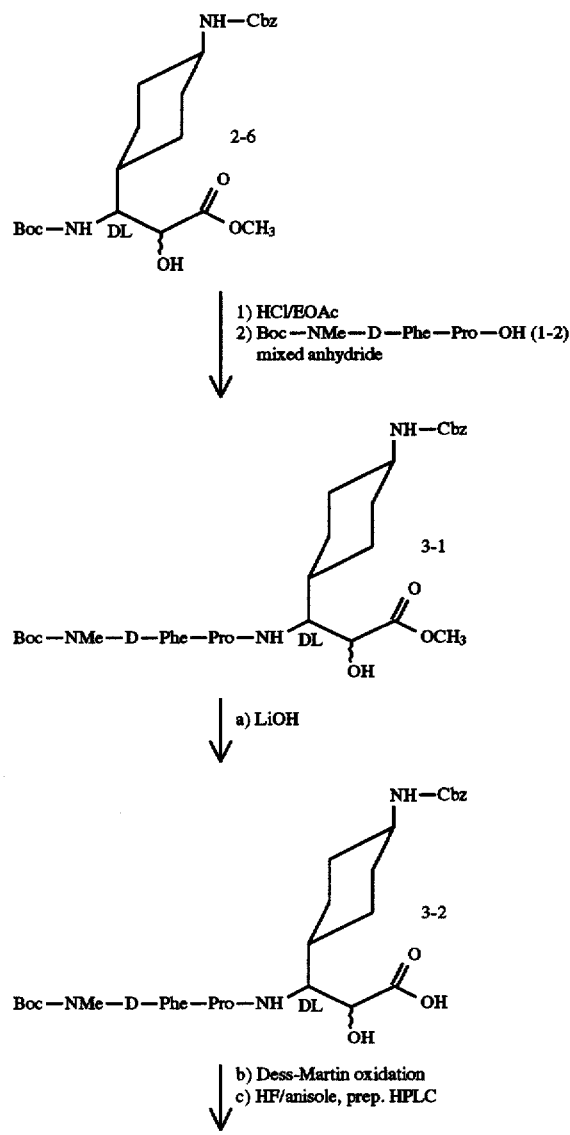

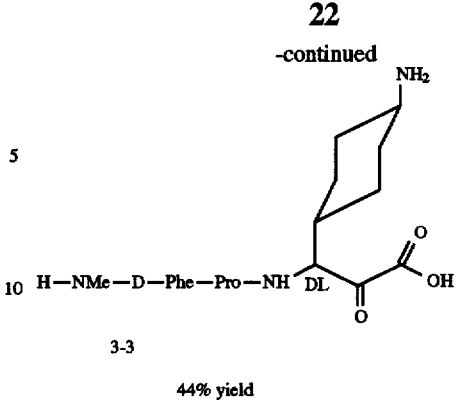

44% yield

Boc-NMe-D-Phe-Pro-t-DL-Acg(Cbz)Ψ[CHOHCO]
—OMe (3-1)

Preparation of the HCl salt of t-DL-Acg(Cbz)Ψ[CHOHCO]—OMe:

A solution of Boc-trans-Acg(Cbz)Ψ[CHOHCO]—OMe (202 mg, 0.448 mmol) in EtOAc (20 ml) was cooled to −25° C. under N$_2$, and gaseous HCl was introduced until saturation, keeping the reaction temperature below −5° C. After 10 min at saturation, the solution was purged with N$_2$ for 45 min, then excess HCl and solvent were removed by evaporation in vacuo to give the oily HCl salt.

Preparations of Boc-NMe-D-Phe-Pro-t-DL-Acg(Cbz)Ψ[CHOHCO—OMe (3-1):

While the deprotection was carded out, a solution of Boc-NMe-D-Phe-Pro-OH (1-2) (187 mg, 0.493 mmol) in 15 ml of CH$_2$Cl$_2$and 3 ml of EtOAc, to which was added 54 µl of NMM, was cooled to −15° C. under N$_2$ and treated with 64 µl of i-butyl chloroformate. After 10 min at −15°, a solution of the above prepared HCl salt in 4 ml of CH$_2$Cl$_2$ was added in portions, alternately with NMM (50 µl), followed by NMM addition (35 µl) to bring the pH to 7 (moistened narrow pH paper). The coupling was followed by TLC (85-15-1.5, CHCl$_3$—MeOH—H$_2$O) to disappearance of nucleophile. After 2 hrs at −10° C., H$_2$O was added, the mixture was stirred for 1 hr, the layers separated, and the organic layer washed with 1×dilute KHSO$_4$ solution, 1×H$_2$O, 1×NaHCO$_3$ solution, and 2×50% saturated NaCl. The organic layer was dried over Na$_2$SO$_4$, filtered and evaporated to dryness. The crude product was purified by chromatography on silica gel, eluting with 99-1-0.1 (CHCl$_3$—MeOH—H$_2$O), and the combined fractions containing product were evaporated in vacuo to give 3-1 as a white solid (275 mg, 87% yield).

TLC: R$_f$=0.45, 0.5 (2 isomers), silica gel, CHCl$_3$—MeOH—H$_2$O (95-5-0.5)

HPLC: retention times=17.2 min and 17.5 min, ratio 46:43, (Vydac C$_{18}$, gradient of 75% A/B to 20% A/B over 30 min, A=0.1% TFA—H$_2$O, B=0.1% TFA—CH$_3$CN Boc-NMe-D-Phe-Pro-t-DL-Acg(Cbz)Ψ[CHOHCO]
—OH (3-2)

A sample of Boc-NMe-D-Phe-Pro-t-DL-Acg(Cbz)Ψ[CHOHCO]—OMe (3-1) (270 mg, 0.38 mmol) dissolved in 17 ml of 1:1(v/v) THF/H$_2$O was treated with 2.2N LiOH (0.22 ml) in portions over 1.5 hrs. keeping the pH at 12-13. After 2.5 hrs., the reaction solution was adjusted to pH 7 with dilute KHSO$_4$ solution, 50 ml of EtOAc and 25 ml of H$_2$O were added, and the aqueous layer was further adjusted to pH 2 with KHSO$_4$ solution. The organic layer was separated and washed twice with 50% saturated NaCl solution, dried over Na₂SO₄, and evaporated in vacuo to give 3-2 (251 mg, 95% yield).

TLC: $R_f$=0.4, silica gel, upper layer of EtOAc—AcOH-i-octane-H₂O (12-2-2-10)

3-2 was oxidized and deprotected, following procedures described in Example 4 below, to yield 3—3.

EXAMPLE 4

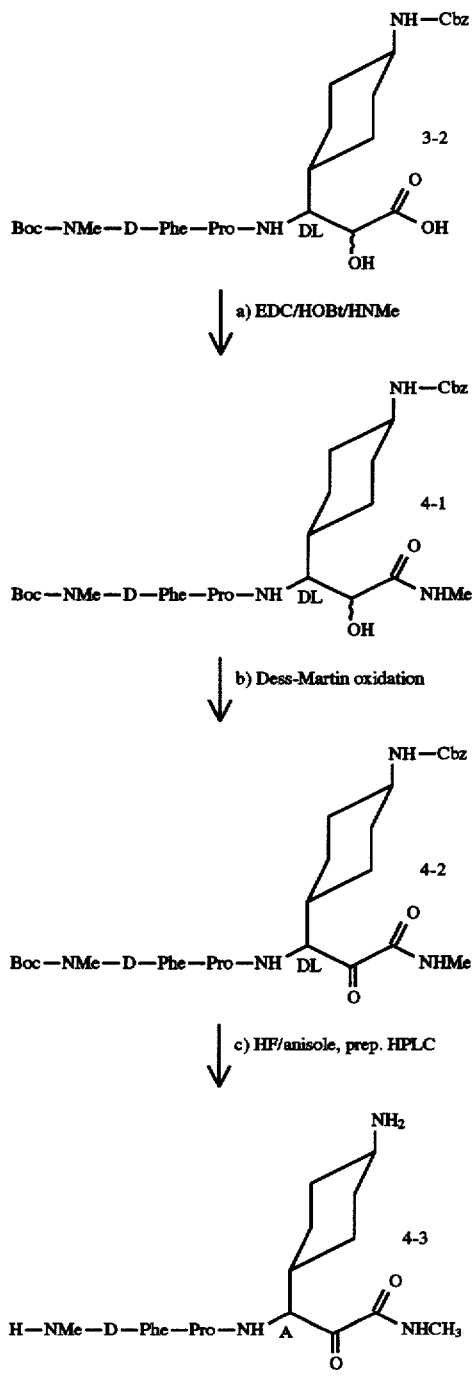

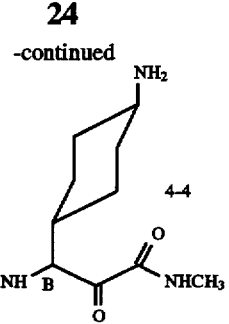

46% yield

Boc-NMe-D-Phe-Pro-t-DL-Acg(Cbz)Ψ[CHOHCO] —NHMe (4-1)

To a solution of Boc-NMe-D-Phe-Pro-t-DL-Acg(Cbz)ΨP [CHOHCO]—OH (3-2) (125 mg, 0.18 mmol) in 6.5 ml of dimethyl acetamide was added 34 mg of 1-hydroxybenzotriazole hydrate (HOBt), 35 µl of NMM and 29 mg of methylamine hydrochloride, and the mixture was stirred for 15 min to attain complete dissolution. To this solution was added 1-(3-dimethylaminopropyl)-3-ethylcarbodiimide hydrochloride (EDC, 51 mg) and the resultant mixture was stirred magnetically for 20 hrs. Water (30 ml) and EtOAc (75 ml) were added, the organic layer was washed with dilute KHSO₄ solution, H₂O, NaHCO₃ solution, and 50% saturated NaCl, dried over Na₂SO₄, filtered, and evaporated in vacuo to yield 4-1(117 mg, 92% yield).

TLC: $R_f$=0.3, silica gel, CHCl₃—MeOH—H₂O (95-5-0.5)

Boc-NMe-D-Phe-Pro-t-DL:Acg(Cbz)Ψ[COCO]—NHMe (4-2)

To a solution of Boc-NMe-D-Phe-Pro-t-DL-Acg(Cbz)Ψ [CHOHCO]—NHMe (4-1) (115 mg, 0.16 mmol) in 9 ml of CH₂Cl₂ was added with magnetic stirring 0.46 g of periodinane (Dess-Martin reagent). After 1 hr., ether (45 ml) was added, followed by the addition with vigorous stirring of a sodium thiosulfate solution (2.0 g in 25 ml of saturated NaHCO₃). After 5 min. both layers were clear, and the ether layer was separated and washed with dilute NaHCO₃, 50% saturated NaCl, dried over Na₂SO₄, and evaporated in vacuo to give crude keto-amide 4-2.

TLC: $R_f$=0.50, silica gel, CHCl₃—MeOH—H₂O (95-5-0.5)

H-NMe-D-Phe-Pro-t-D-AcgΨ[COCO]—NHMe (4-3) and H-NMe-D.-Phe-Pro-t-L-AcgΨ[COCO]—NHMe (4—4)

A solution of Boc-NMe-D-Phe-Pro-t-DL-Acg(Cbz)Ψ [COCO]—NHMe (4-2) (125 mg) in 4 ml of CH₂Cl₂ in an HF reactor vessel (Kel-F) was freed of solvent by N₂ purging, and the residue in 1.2 ml of anisole was evacuated to remove residual CH₂Cl₂. Approximately 12 ml of HF was condensed into the reaction vessel at −70° C. After 1.25 hr of stirring at 0°–5°, the HF was removed in vacuo, and 20 ml of ether, followed by 20 ml of petroleum ether, were added to the residue. The supernatant was decanted into a sintered glass funnel, and the tacky residue was washed with 3 portions of 1:1 (v/v) ether/petroleum ether, decanting each as above. After drying in a stream of N₂, the residue in the vessel was dissolved in 25 ml of H₂O, pouring the solution through the above sintered funnel to assure complete recovery of product. The filtrate which contained the two diastereomeric products was charged directly onto the preparative HPLC Waters Prep-Pak C₁₈ column using a gradient elution system of 100% A to 60% A/B over 120 min, at a flow rate of 80 ml/min. The later eluting peak of the two isomers was the more potent thrombin inhibitor and had the L-configuration (4—4) at Acg center.

HPLC: retention times=16.7 min (D) and 18.5 min (L), Vydac $C_{18}$, gradient of 100% A to 65% A/B over 30 min, A=0.1% TFA—$H_2O$, B=0.1% TFA—$CH_3CN$ FABMS for both isomers: 472 (M+H), 504 (M+MeOH), calcd. mol. wt.=472

In a similar manner are prepared the following:

PhCH$_2$CH$_2$CO-Pro-t-D-AcgΨ[COCO]—NHMe (4-3-1) and PhCH$_2$CH$_2$CO-Pro-t-L-AcgΨ[COCO]—NHMe (4-4-1) via coupling of PhCH$_2$CH$_2$CO-Pro-OH (1-2-1) with the aforesaid HCl salt of t-DL-Acg(Cbz)Y[CHOHCO]—OMe and processing (Example 3).

3,4-Dichloro-PhCH$_2$CH$_2$CO-Pro-t-D-AcgΨ[COCO]—NHMe (4-3-2) and 3,4-dichloro-PhCH$_2$CH$_2$CO-Pro-t-L-AcgΨ[COCO]—NHMe (4-4-2) via coupling of 3,4-Dichloro-PhCH$_2$CH$_2$CO-Pro-OH (1-2-2) with the aforesaid HCl salt of t-DL-Acg(Cbz)Ψ[CHOHCO]—OMe and processing (Example 3).

ChxCH$_2$CH$_2$CO-Pro-t-D-AcgΨ[COCO]—NHMe (4-3-3) and ChxCH$_2$CH$_2$CO-Pro-t-L-AcgΨ[COCO]—NHMe (4-4-3) via coupling of ChxCH$_2$CH$_2$CO-Pro-OH (1-2-3) with the aforesaid HCl salt of t-DL-Acg(Cbz)Ψ[CHOHCO]—OMe and processing (Example 3).

Ph$_2$CHCH$_2$CO-Pro-t-D-AcgΨ[COCO]—NHMe (4-3-4) and Ph$_2$CHCH$_2$CO-Pro-t-L-AcgΨ[COCO]—NHMe (4-4-4) via coupling of Ph$_2$CHCH$_2$CO-Pro-OH (1-2-4) with the aforesaid HCl salt of t-DL-Acg(Cbz)Ψ[CHOHCO]—OMe and processing (Example 3).

(Chx)$_2$CHCH$_2$CO-Pro-t-D-AcgΨ[COCO]—NHMe (4-3-5) and (Chx)$_2$CHCH$_2$CO-Pro-t-L-AcgΨ[COCO]—NHMe (4-4-5) via coupling of (Chx)$_2$CHCH$_2$CO-Pro-OH (1-2-5) with the aforesaid HCl salt of t-DL-Acg(Cbz)Ψ[CHOHCO]—OMe and processing (Example 3).

9-Hydroxyfluorene-9-carboxy-pro-t-D-AcgΨ[COCO]—NHMe (4-3-6) and 9-Hydroxyfluorene-9-carboxy-Pro-t-L-AcgΨ[COCO]—NHMe (4-4-6) via coupling of 9-Hydroxyfluorene-9-carboxy-Pro-OH (1-2-6) with the aforesaid HCl salt of t-DL-Acg(Cbz)Y[CHOHCO]—OMe and processing (Example 3).

H-NMe-D-Phe-Pro-t-D-AcgΨ[COCO]-azetidine amide (4-3-7) and H-NMe-D-Phe-Pro-t-L-AcgΨ[COCO]-azetidine amide (4-4-7) via coupling of Boc-NMe-D-Phe-Pro-t-DL-Acg(Cbz)Y[CHOHCO]—OH (3-2) with azetidine ($C_4H_7N$) and processing (Example 3).

H-NMe-D-Phe-Pro-t-D-AcgΨ[COCO]-benzylamide (4-3-8) and H-NMe-D-Phe-Pro-t-L-AcgΨ[COCO]-benzylamide (4-4-8) via coupling of Boc-NMe-D-Phe-Pro-t-DL-Acg(Cbz)Y[CHOHCO]—OH (3-2) with benzylamine (PhCH$_2$NH$_2$) and processing (Example 3).

In vivo studies of two of the compounds of the invention (compound 4-4, H-NMe-D-Phe-Pro-t-L-AcgY[COCO]—NHMe and compound 3-3, H-NMe-D-Phe-Pro-t-DL-AcgY[COCO]—OH) were carried out using the following rat ferric chloride assay. In the assay, male Sprague-Dawley rats (body weights 200–350 grams) were anesthetized with dial-urethane solution (0.1 ml/100 gm body weight i.p.), and a lateral tail vein was cannulated with a 23 gauge needle connected to a 12 inch length of PE50 robing. The robing was attached to a 3-way valve by a tubing adapter. Saline (control) or test compound, as appropriate, was administered via the tail vein catheter. A tracheostomy was performed with a 0.75 inch length of PE205 tubing. The right carotid artery was exposed and a 1.3 mm diameter Doppler flow probe was placed on the vessel. Body temperature was maintained at 37° C. using a heat lamp.

Rats (8–10/group) were randomized to continuous intravenous infusions of saline or test compound administered via the tail vein at a rate of 0.028 ml/min. Treatment infusions were initiated 60 min before the placement of a 3 mm square piece of Whatman No. 1 filter paper saturated with 35% $FeCl_3$ onto the exposed carotid artery distal to the flow probe. Treatment infusions were continued for an additional 90 minutes after the application of $FeCl_3$ (total infusion duration 150 minutes) if thrombotic occlusions did not occur, or were terminated 30 minutes after thrombotic occlusion of the vessel. Time to occlusion was defined as the time from application of FeCl3 to thrombotic occlusion of the vessel. At the termination of the study (90 minutes after application of $FeCl_3$ in animals which did not occlude, or at 30 minutes after thrombotic occlusion), 3 ml blood samples were drawn by cardiac puncture into 0.3 ml of 3.8% sodium citrate.

The results show that the compounds prevent thrombotic occulsions.

| | FeCl$_3$ induced arterial thrombosis in rats | |
|---|---|---|
| Compound | Incidence of occlusion | Minutes to occulsion of those occluding |
| Saline (control) | 24/27 | 18–20 |
| H—NMe—D—Phe—Pro—NH [structure] (4-4) | 3/4 (1 µg/kg/min i.v.)<br>2/4 (5 µg/kg/min i.v.)<br>0/4 (10 µg/kg/min i.v.) | 21<br>18–20<br>— |

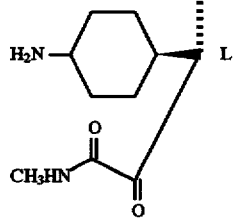

-continued

FeCl₃ induced arterial thrombosis in rats

| Compound | Incidence of occlusion | Minutes to occulsion of those occluding |
|---|---|---|
| H—NMe—D—Phe—Pro—NH (3-3) | 3/4 (10 µg/kg/min i.v.) | 22–24 |
|  | 0/4 (20 µg/kg/min i.v.) | — |
|  | 0/4 (50 µg/kg/min i.v.) | — |

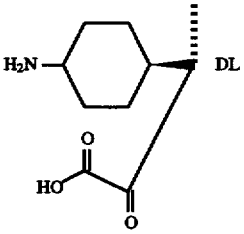

Occlusion occurred in 24 of 27 subjects during administration of saline. Compounds of the invention, depending on rate of infusion of test compound, prevented occulsion in some or all of 4 subjects tested. The in vivo study shows that compounds of the invention prevent fibrin clot formation by inhibiting thrombin catalyzed conversion of fibrinogen to fibrin, and are useful for preventing and treating thrombotic conditions including deep vein thrombosis, unstable angina, and myocardial infarction.

Oral bioavaliability studies of compound 4—4 showed that the compound was available in three species. Concentration was determined in animal plasma after oral (gastric lavage) administration.

Rats were anesthetized and instrumented with indwelling left jugular vein and left carotid artery catheters for test agent administration and for serial blood sampling, respectively. One day after instrumentation, blood samples were obtained before saline or inhibitor administration and at increasing time points after the oral administration.

In dogs, the test agent was administered intravenously as a bolus or orally by gastric lavage. For intravenous studies, the sterile agent is dissolved in sterile 0.9% saline and administered via 19 g butterfly, usually via the saphenous vein. For oral studies, the sterile agent was dissolved in sterile water and administered via a feeding tube. Blood samples (5 cc each) were collected with a plastic syringe containing 3.8% sodium citrate via venipuncture (at sites other than that of drug administration) for drug plasma levels and thrombin clotting time assay. Dogs were allowed to recover 14 days before being used again in a similar protocol.

In monkeys, the test agent was administered intravenously as a bolus or orally by pediatric nasogastric tube. For intravenous studies, the sterile agent was dissolved in sterile 0.9% saline and administered via 21 g butterfly, usually via the brachial vein. For oral studies, the sterile agent was dissolved in sterile water and administered via a nasogastric tube. Blood samples (4 cc each) were collected with a plastic syringe containing 3.8% sodium citrate via venipuncture (at sites other than that of drug administration) for drug plasma levels and thrombin clotting time assay. The monkeys were given water ad lib. Monkeys were allowed to recover 14 days before being used again in a similar protocol.

Thrombin inhibitor concentrations in plasma were determined by the inactivation of a known amount of thrombin (where [thrombin]$>>K_i$ of inhibitor) from an aliquot of acid-neutralized rat plasma. 0.25 ml of rat platelet poor plasma was mixed with 25 µl of 3M perchloric acid. The sample was centrifuged (14,000×g for 10 minutes) and 0.2 ml of the supernatant was neutralized with 0.43 ml of 1M Tris/0.15M NaCl/0.1% PEG 8000 pH 7.8. 50–100 µl of acid-neutralized rat plasma was mixed with 50–100 µl of 0.03–3 µM thrombin. After equilibration, 5–10 µl of 5 mM Sar-Pro-Arg-pna (for <0.1 µM thrombin) or Spectrozyme PCa (for >0.1 µM thrombin) was added. The observed inhibited velocity was compared to inhibited velocities from a standard curve generated from rat plasma containing known amounts of inhibitor treated in an identical manner. The table below summarizes the results from these studies.

Bioavailability of 4-4 in rats, dogs, and rhesus monkeys

| Animal | % bioavailable | ± SD | % Range | n |
|---|---|---|---|---|
| rat | 5 | 4 | 1 to 11 | 7 |
| dog | 8 | 5 | 2 to 15 | 4 |
| rhesus | 5 | 3 | 2 to 8 | 4 |

The results show that compounds of the invention are orally bioavailable for inhiting thrombin.

Thrombin Inhibitors—Therapeutic Uses

Anticoagulant therapy is indicated for the treatment and prevention of a variety of thrombotic conditions, particularly deep vein thrombosis, pulmonary embolism, cerebral thrombosis associated with atrial fibrillation, coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts.

The thrombin inhibitors can be administered in the form of a depot injection or implant preparation which may be formulated in such a s manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carders to which the compound molecules are coupled. The thrombin inhibitors may also be coupled with soluble polymers as targetable drag carders. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drag, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.2 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of a tablet or capsule, the active drag component can be combined with an oral, nontoxic, pharmaceutically acceptable, inert carder such as lactose, starch, sucrose, glucose, methyl cellulose, magnesium stearate, dicalcium phosphate, calcium sulfate, mannitol, sorbitol and the like; for oral administration in liquid form, the oral drag components can be combined with any oral, non-toxic, pharmaceutically acceptable inert carder such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various vascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

What is claimed is:

1. Compounds of the formula

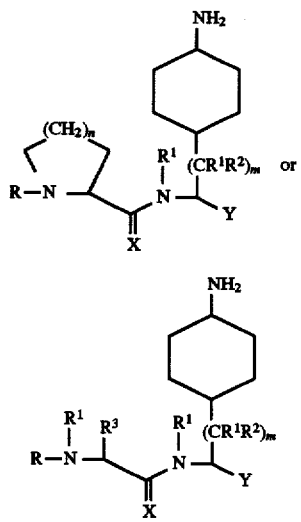

wherein:
  m=0 or 1;
  n=0,1, or 2;
  X=O or $H_2$;
  R=arylsulfonyl, aminoacyl, acylaminoacyl, N-$C_{1-3}$alkyl aminoacyl, acyl-N-$C_{1-3}$alkylaminoacyl, arylacyl, aryl$C_{1-3}$alkanoyl, hydroxyacyl, aryloxycarbonyl, $C_{1-3}$alkyloxycarbonyl, or

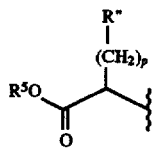

where p is 0, 1, or 2;

R"=aryl, heteroaryl, $C_{5-11}$carbomonocyclic, or $C_{5-11}$carbobicyclic;

$R^1$=H or $CH_3$;

$R^2$=H or $CH_3$;

$R^3$=H, $C_{1-3}$alkyl, hydroxy$C_{1-3}$alkyl, carboxy$C_{1-3}$alkyl, amino$C_{1-3}$alkyl, guanido$C_{1-3}$alkyl, aryl or substituted aryl, arylmethyl, $C_{3-8}$ cycloalkylmethyl, or $C_{3-8}$ cycloalkyl;

$Y=CONR^5R^6$, $COCO_2R^4$, $COCH_2H$, or COCO—Q, wherein

Q=

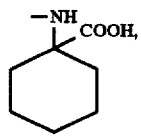

$NR^5R^6$, or

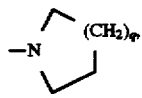

where q is 0, 1 or 2;

$R^4$=$C_{1-3}$alkyl or aryl$C_{1-3}$alkyl;

$R^5$=H, $C_{1-3}$alkyl or aryl$C_{1-3}$alkyl;

$R^6$=H, $C_{1-3}$alkyl or aryl$C_{1-3}$alkyl;

$R^7$=H, $C_{1-3}$alkyl or aryl$C_{1-3}$alkyl; and $R^8$=H, $C_{1-3}$alkyl or aryl$C_{1-3}$alkyl, and pharmaceutically acceptable salts thereof.

2. Compounds of claim 1 having the formula

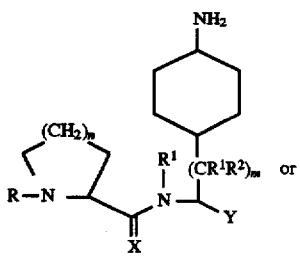

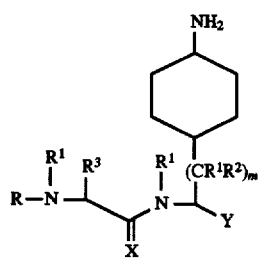

wherein:

n=0, 1, or 2;

m=0 or 1;

R=D-phenylalanine, D-Nal1, D-Nal2, D-cyclohexylalanine, D-tyrosine, β-3-benzothienyl-D-alanine, D-3,4-$Cl_2$-phenylalanine, 3-phenylpropionyl, 3,4-dichlorophenylpropionyl, 3-cyclohexylpropionyl, 3,3-diphenylpropionyl, 5-dicyclohexylpropionyl, and 9-hydroxy-9-carboxyfluorene, or N-methyl derivatives thereof, or

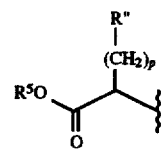

where p is 0, 1, or 2;

$R^1$=H;

$R^3$=H or cyclohexyl;

X=O or $H_2$; and $Y=CONH_2$, $COCO_2H$, $COCONHCH_3$, $COCONHCH_2Ph$,

and pharmaceutically acceptable salts thereof.

3. Compounds of claim 2 having the formula

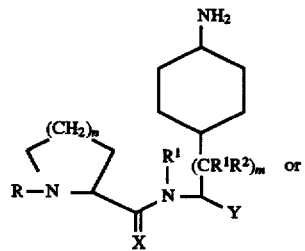

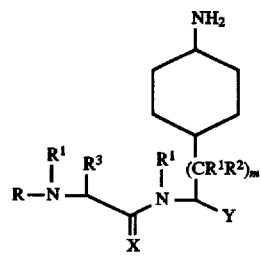

wherein:

n=0, 1, or 2;

m=0 or 1;

R=D-phenylalanine, D-Nal1, D-Nal2, D-cyclohexylalanine, D-tyrosine, β-3-benzothienyl-D-alanine, or D-3,4-$Cl_2$-phenylalanine, or N-methyl derivatives thereof, or

33

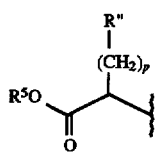

where p is 0, 1, or 2;
R¹=H;
R³=H or cyclohexyl;
X=O or H²; and
Y=CONH₂, COCO₂H, COCONHCH₃, COCONHCH₂Ph,

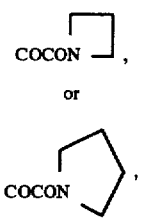

and pharmaceutically acceptable salts thereof.
4. Compounds of claim 3 having the formula:

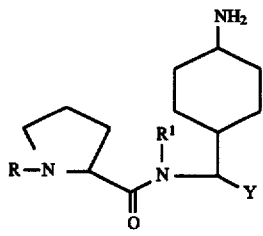

or

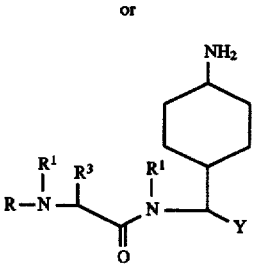

wherein:

R=N-methyl-D-phenylalanine, N-methyl-2-naphthyl-D-alanine, N-methyl-1-naphthyl-D-alanine, N-methyl-D-cyclohexylalanine, N-methyl-D-3,4-Cl₂-D-phenylalanine, or

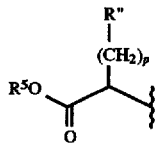

where p is 0, 1, or 2;
R¹=H;
R³=H, cyclohexyl; and

34

Y=CONH₂, COCO₂H, COCONHCH₃,

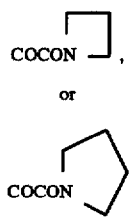

and pharmaceutically acceptable salts thereof.
5. Compounds of claim 2 selected from the group consisting of:

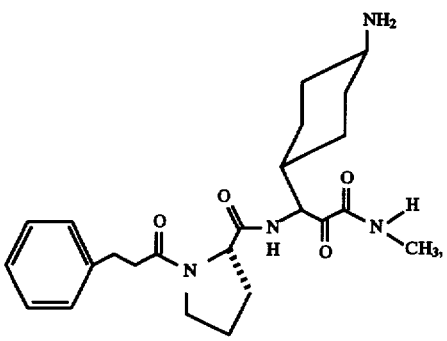

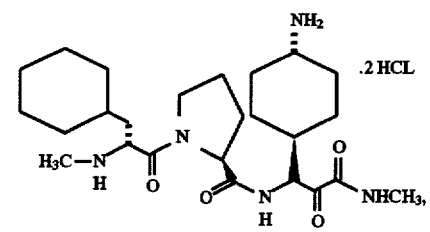

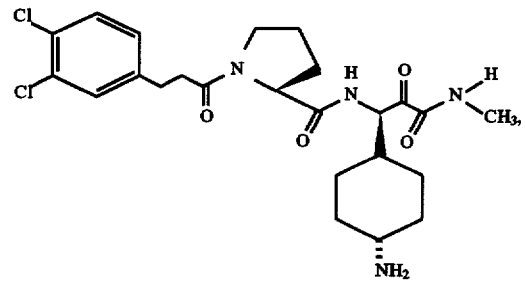

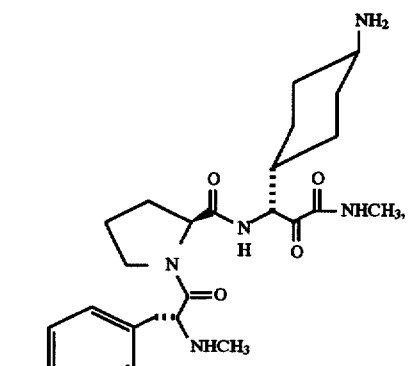

35
-continued
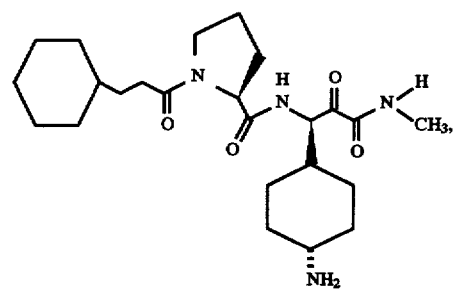
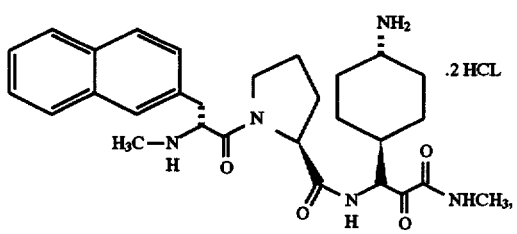
.2 HCL
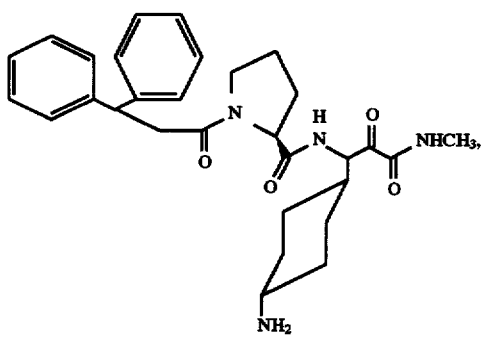
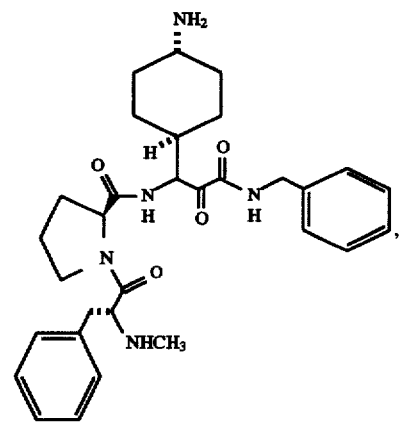
36
-continued
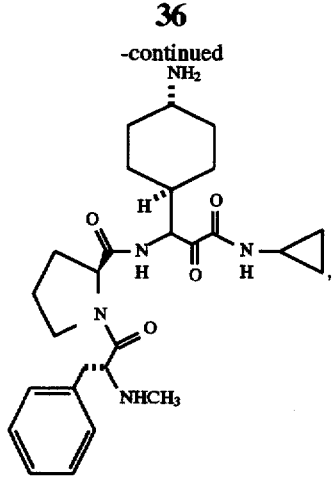
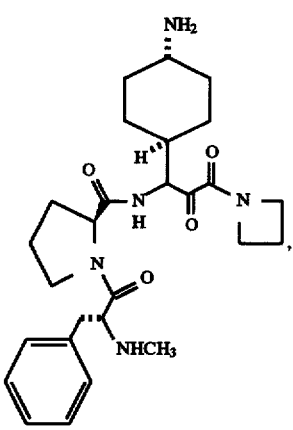
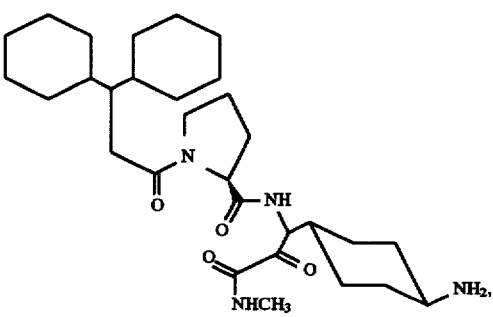
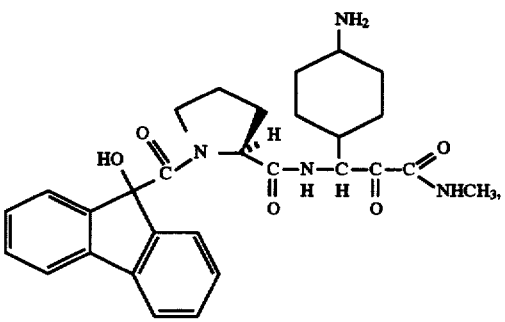
and pharmaceutically acceptable salts thereof.
6. Compounds of claim 4 selected from the group consisting of:

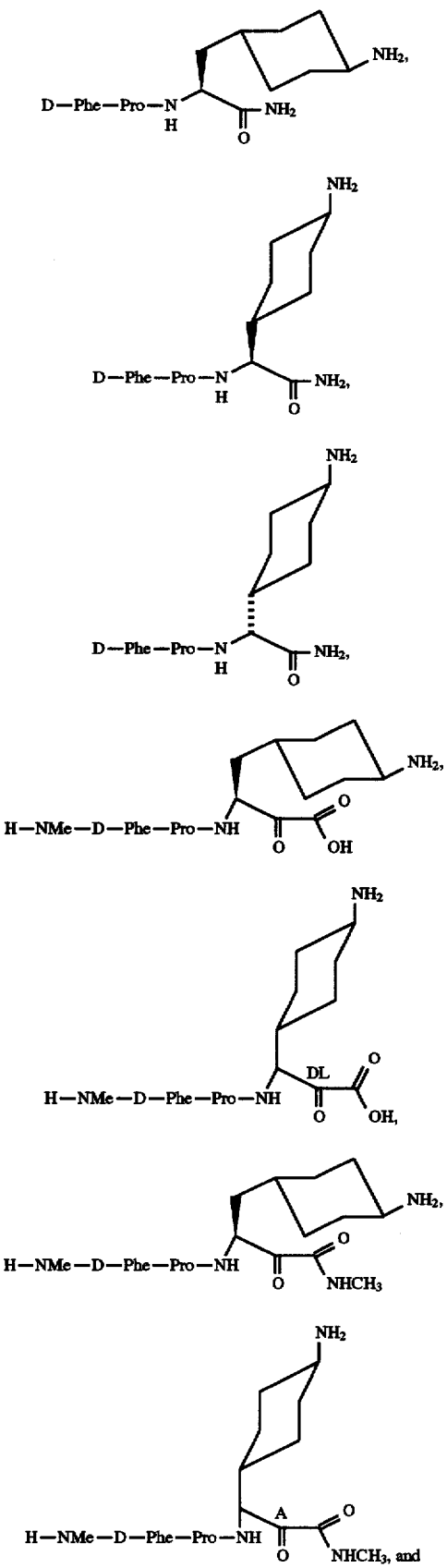

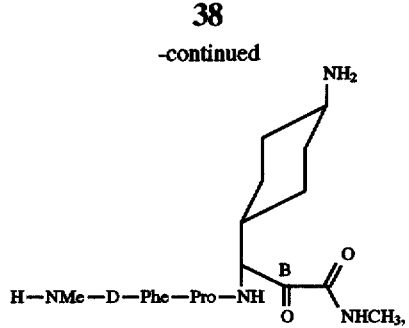

and pharmaceutically acceptable salts thereof.

7. Compounds of the formula

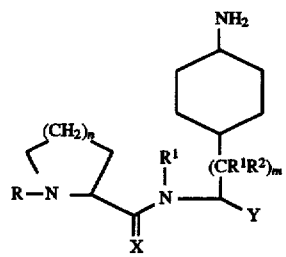

wherein:
m=0 or 1;
n=0, 1, or 2;
X=O or $H_2$;
R=arylsulfonyl, aminoacyl, acylaminoacyl, N-$C_{1-3}$alkyl aminoacyl, acyl-N-$C_{1-3}$alkylaminoacyl, arylacyl, aryl $C_{1-3}$alkanoyl, hydroxyacyl, aryloxycarbonyl, $C_{1-3}$alkyloxycarbonyl, or

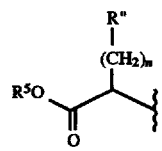

where p is 0, 1, or 2;
R"=aryl, heteroaryl, $C_{5-11}$ carbomonocyclic, or $C_{5-11}$ carbobicyclic;
$R^1$=H or $CH_3$;
$R^2$=H or $CH_3$;
Y=$CONR^5R^6$, $COCO_2R^4$, $COCO_2H$, or COCO—Q, wherein
Q=

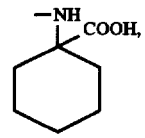

$NR^5R^6$, or

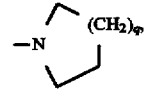

where q is 0, 1 or 2;
$R^4$=$C_{1-3}$alkyl or aryl$C_{1-3}$alkyl;

$R^5$=H, $C_{1-3}$alkyl or aryl$C_{1-3}$alkyl;
$R^6$=H, $C_{1-3}$alkyl or aryl$C_{1-3}$alkyl;
$R^7$=H, $C_{1-3}$alkyl or aryl$C_{1-3}$alkyl; and
$R^8$=H, $C_{1-3}$alkyl or aryl$C_{1-3}$alkyl,
and pharmaceutically acceptable salts thereof.

8. Compounds of the formula

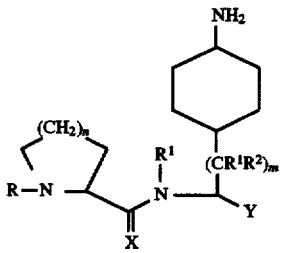

wherein:
m=0 or 1;
n=0, 1, or 2;
X=O or $H_2$;
R=arylsulfonyl, aminoacyl, acylaminoacyl, N-$C_{1-3}$alkyl aminoacyl, acyl-N-$C_{1-3}$alkylaminoacyl, arylacyl, aryl $C_{1-3}$alkanoyl, hydroxyacyl, aryloxycarbonyl, $C_{1-3}$alkyloxycarbonyl;
$R^1$=H or $CH_3$;
$R^2$=H or $CH_3$;
Y=CON$R^5R^6$, COCO$_2R^4$, COCO$_2$H, or COCO—Q, wherein

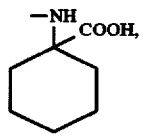

$NR^5R^6$, or

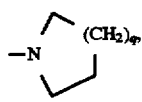

where q is 0, 1 or 2;
$R^4$=$C_{1-3}$alkyl or aryl$C_{1-3}$alkyl;

$R^5$=H, $C_{1-3}$alkyl or aryl$C_{1-3}$alkyl;
$R^6$=H, $C_{1-3}$alkyl or aryl$C_{1-3}$alkyl;
$R^7$=H, $C_{1-3}$alkyl or aryl$C_{1-3}$alkyl; and
$R^8$=H, $C_{1-3}$alkyl or aryl$C_{1-3}$alkyl,
and pharmaceutically acceptable salts thereof.

9. A composition for inhibiting thrombin in blood comprising a compound of claim 1 and a pharmaceutically acceptable carrier.

10. A composition for inhibiting formation of blood platelet aggregates in blood comprising a compound of claim 1 and a pharmaceutically acceptable carrier.

11. A composition for inhibiting formation of fibrin in blood comprising a compound of claim 1 and a pharmaceutically acceptable carrier.

12. A composition for inhibiting thrombus formation in blood comprising a compound of claim 1 and a pharmaceutically acceptable carrier.

13. A method for inhibiting thrombin in blood comprising adding to the blood a composition of claim 9.

14. A method for inhibiting formation of blood platelet aggregates in blood comprising adding to the blood a composition of claim 10.

15. A method for inhibiting formation of fibrin in blood comprising adding to the blood a composition of claim 11.

16. A method for inhibiting thrombus formation in blood comprising adding to the blood a composition of claim 12.

17. A method for treating myocardial infarction in a mammal, comprising administering to the mammal a composition of claim 9.

18. A method for treating thrombotic stroke in a mammal, comprising administering to the mammal a composition of claim 9.

19. A method for treating embolic stroke in a mammal, comprising administering to the mammal a composition of claim 9.

20. A method for treating deep vein thrombosis in a mammal, comprising administering to the mammal a composition of claim 9.

21. A method for treating disseminated intravascular coagulation in a mammal, comprising administering to the mammal a composition of claim 9.

22. A method for treating reocclusion or restenosis of recanalized vessels in a mammal, comprising administering to the mammal a composition of claim 9.

* * * * *